US00PP08003P

United States Patent [19]

Zaiger et al.

[11] Patent Number: Plant 8,003

[45] Date of Patent: Oct. 13, 1992

[54] PEACH TREE "SEPTEMBER SNOW"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 694,958

[22] Filed: Apr. 29, 1991

[51] Int. Cl.[5] ..... A01H 5/00

[52] U.S. Cl. ..... Plt./42.1

[58] Field of Search ..... Plt./42

*Primary Examiner*—James R. Feyrer

[57] ABSTRACT

The new and distinct variety of peach tree has the following unique combination of desirable features:

1. Heavy and regular production of white flesh freestone fruit.
2. Fruit with large size and very good flavor and eating quality.
3. Fruit with firm flesh and good handling and shipping qualities.
4. Large tree size with vigorous upright growth.
5. Maturity of fruit in the late season.

1 Drawing Sheet

ORIGIN OF THE VARIETY

The present new variety of peach tree was developed by us in our experimental orchard located near Modesto, Calif., as a second generation cross between a selected seedling and White Lady Peach (U.S. Plant Pat. No. 5,821). The selected seedling was the maternal parent, which originated from a cross of Royal Gold Peach (U.S. Plant Pat. No. 2,663) with a late maturing nectarine seedling selected from open pollinated Red Grand Nectarine (U.S. Plant Pat. No. 1,060) seedlings. We grew and maintained a large group of these second generation seedlings under close observation and the present variety exhibited the distinctive desirable characteristics described above and was selected for reproduction and commercialization.

ASEXUAL REPRODUCTION OF THE VARIETY

The present variety of peach tree was asexually propagated by budding, as performed by us in our experimental orchard located near Modesto, Calif., and shows that said characteristics of the tree and its fruit are established and transmitted through succeeding propagations and come true to the original tree in all respects.

SUMMARY OF THE VARIETY

A new and distinct variety of peach tree which is of large size, vigorous upright growth and productive and regular bearer of large, white flesh, freestone fruit with very good flavor and eating quality. Characterized as to its novelty by its uniform size of fruit throughout the tree, its firm flesh, its good handling and shipping qualities and its ripening in the late maturity season, approximately 6 weeks after White Lady Peach (U.S. Plant Pat. No. 5,821).

DESCRIPTION OF THE PHOTOGRAPHS

The accompanying photographic illustrations show typical specimens of the foliage and fruit of the present new variety of peach tree. The upper and lower surface of the leaves are shown as well as the exterior and sectional view of the fruit showing flesh coloration and a stone remaining in place. The photographic illustrations were taken shortly after being picked at maturity (firm ripe) and the colors are as nearly true as is reasonably possible in a color representation of this type.

DESCRIPTION OF THE VARIETY

The following is a detailed botanical description of the new and distinct variety of peach tree, its flowers, fruit and foliage, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearer.*—Regular.
- *Production.*—Productive.

Trunk:
- *Size.*—Medium stocky.
- *Texture.*—Medium shaggy.
- *Color.*—Brown to grayish brown (5-E-3) to (5-E-5).

Branches:
- *Size.*—Medium.
- *Texture.*—Smooth to medium rough.
- *Lenticels.*—Medium size. Medium number.
- *Color:*—New growth — reddish brown to brown (8-E-4) to (8-E-6). Mature growth — light brown to brown (6-E-4) to (6-E-5).

Leaves:
- *Size.*—Large. Average length — 6". Average width — 1⅝".
- *Form.*—Varies from lanceolate to oblanceolate. Pointed.
- *Margin.*—Crenate.
- *Thickness.*—Medium.
- *Petiole.*—Medium length. Medium thickness.
- *Surface.*—Smooth.
- *Glands.*—Reniform. Number varies from 0 to 4. Average number 2. Medium size. Located on base of leaf blade and upper portion of petiole.

*Color.*—Upper surface — green to dark green (27-F-6) to (27-F-8). Lower surface — pale green to pastel green (27-E-3) to (27-E-4).

Flower buds:

*Size.*—Medium.

*Length.*—Medium.

*Form.*—Plump.

*Pubescence.*—Pubescent.

Flowers:

*Size.*—Medium — non-showy.

*Blooming period.*—Mar. 2, 1990 to Mar. 8, 1990. Varies slightly with climatic conditions.

*Pollen.*—Present — self fertile.

*Color.*—Pink.

Fruit:

*Maturity when described.*—Firm Ripe.

*Date of first picking.*—Aug. 25, 1990.

*Date of last picking.*—Sep. 2, 1990.

*Size.*—Large. Average diameter axially — 3¼" to 3½". Average transversely in suture plane 3¼" to 3½".

*Form.*—Nearly globose, majority of fruit slightly enlarged near suture.

*Suture.*—Usually rounded, extends from base to apex.

*Ventral surface.*—Rounded to extending slightly outward in or slightly to one side of suture.

*Apex.*—Varies from round to slight pistil point.

*Base.*—Retuse, usually more retuse on the fruit opposite the suture line.

*Cavity.*—Moderately rounded to elongated in suture plane. Average depth — ½". Average breadth — ⅞".

Flesh:

*Ripens.*—Uniform, evenly.

*Texture.*—Firm.

*Fibers.*—Moderate number, small, tender.

*Juice.*—Moderate.

*Amygdalin.*—Undetected.

*Aroma.*—Moderate.

*Eating quality.*—Very good.

*Flavor.*—Very good, sub-acid, mild and sweet.

*Color.*—White to oyster shell white (1-A-1) to (1-A-2). Pit Cavity — red to cocks comb red (10-A-7) to (10-B-7), with red extending into flesh in some areas around pit cavity.

Skin:

*Thickness.*—Medium.

*Texture.*—Medium — tenacious to flesh.

*Down.*—Moderate, medium length.

*Tendency to crack.*—None.

*Color.*—White to yellowish white ground color (3-A-1) to (3-A-2). Pale red to light red blush (10-A-4) to (10-A-7).

Stone:

*Type.*—Freestone.

*Size.*—Large. Average length — 1½". Average breadth — 1 1/16". Average thickness — ⅝".

*Form.*—Oval to ovoid.

*Base.*—Rounded, varies from rounded to straight.

*Apex.*—Nearly round, only slight pistil point.

*Sides.*—Equal to unequal.

*Surface.*—Irregularly furrowed toward apex, pitted toward base. Ridges usually rounded. Pit cavities vary from slightly elongated to round.

*Tendency to split.*—None.

*Color.*—Brown to reddish brown (8-E-8) to (8-F-8).

Use: Dessert.

*Markets.*—Local and long distance.

Keeping quality: Good.

Shipping quality: Good.

The present peach tree, its flowers and fruit herein described may vary in slight detail due to climatic, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous upright growth and being a productive and regular bearer of large size, white flesh fruit with firm flesh, good handling and shipping qualities; the fruit is further characterized by having very good flavor and eating quality, being nearly uniform in size throughout the tree and maturing in the late season approximately 6 weeks after White Lady Peach (U.S. Plant Pat. No. 5,821).

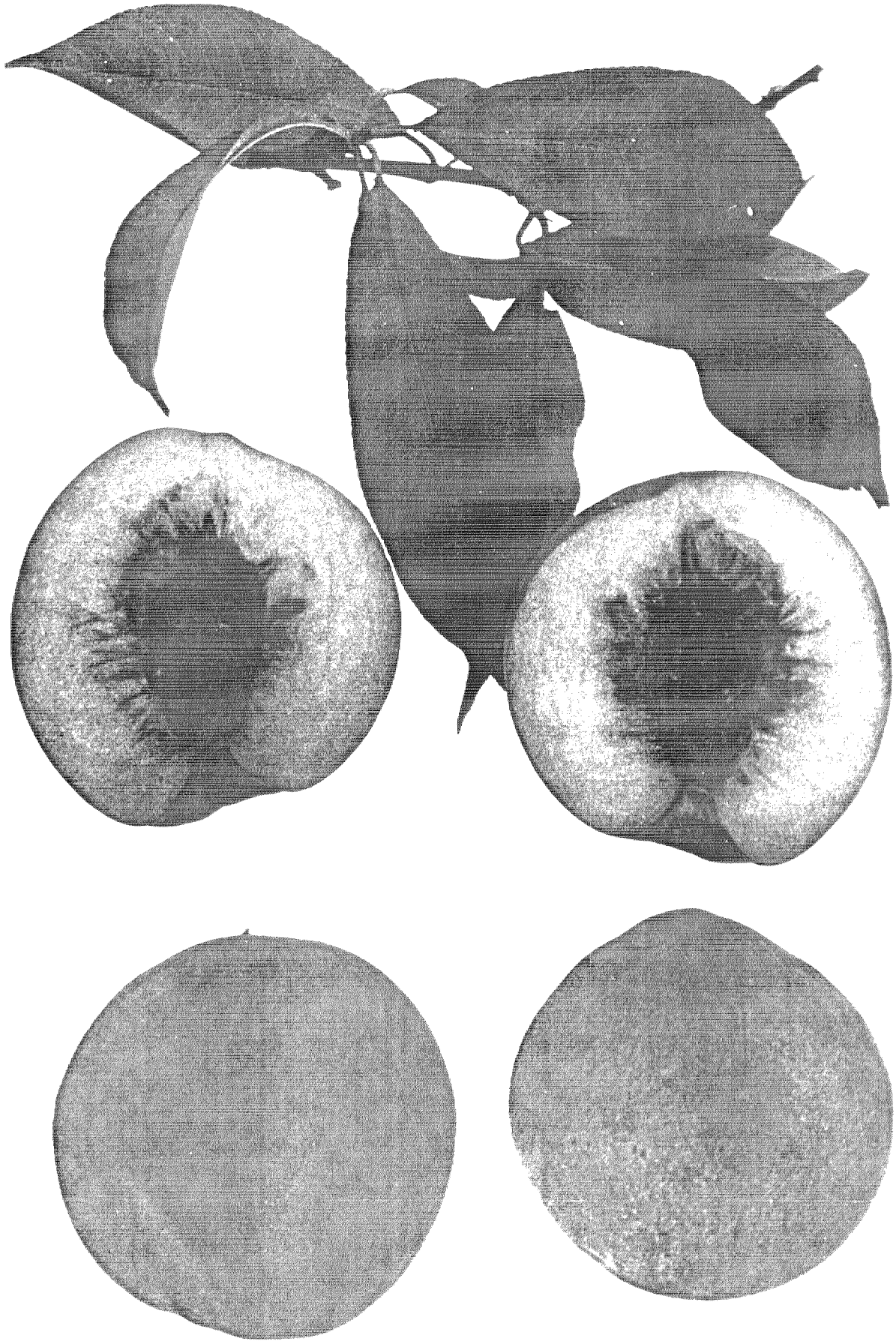

* * * * *